United States Patent [19]
Freeman

[11] Patent Number: 5,100,226
[45] Date of Patent: Mar. 31, 1992

[54] DIFFRACTIVE OPHTHALMIC LENS FOR CORRECTING ASTIGMATISM

[75] Inventor: Michael H. Freeman, Clwyd, United Kingdom

[73] Assignee: Pilkington Visioncare Holdings Inc., Menlo Park, Calif.

[21] Appl. No.: 452,630

[22] Filed: Dec. 19, 1989

[30] Foreign Application Priority Data

Dec. 21, 1988 [GB] United Kingdom ............... 8829819

[51] Int. Cl.$^5$ ................. G02C 7/04; G02B 27/42; A61F 2/16
[52] U.S. Cl. ................. 351/160 R; 351/161; 359/565; 359/569; 359/570; 359/571; 359/575; 623/6
[58] Field of Search ............... 351/160 R, 160 H, 161, 351/162; 350/162.17, 162.20, 162.21, 162.22, 162.23, 162.24; 623/6; 359/565, 569, 570, 571, 575

[56] References Cited

U.S. PATENT DOCUMENTS

| | | | |
|---|---|---|---|
| 3,973,850 | 8/1976 | Povey | 350/3.7 X |
| 3,985,443 | 10/1976 | Danielsson et al. | 350/162.21 X |
| 4,162,122 | 7/1979 | Cohen | 351/161 |
| 4,642,112 | 2/1987 | Freeman | 351/161 X |

FOREIGN PATENT DOCUMENTS

2129157  2/1986  United Kingdom .

OTHER PUBLICATIONS

"Elliptical and hyperbolic zone plates," C. Gomez-Reino et al., Applied Optics, vol. 19, No. 9, May 1980, pp. 1541-1545, New York.
"Diffraction Characteristics of Square Zone Plates," L. J. Janicujevic, Journal of Optics, vol. 13, Aug. 1982, pp. 199-205, Paris.
"Diffraction of Gaussian Beams Through Different Types of Zone Plates," L. J. Janicijevic, Journal of Optics, vol. 18, No. 1, 1987, pp. 23-25, 42, Paris.

*Primary Examiner*—Scott J. Sugarman
*Attorney, Agent, or Firm*—Burns, Doane, Swecker & Mathis

[57] ABSTRACT

An artificial eye lens such as a contact lens or intra-ocular lens corrects astigmatism by two sets of substantially linear parallel zones arranged to diffract light predominantly into one order at one orientation, the spacing of the zones diminishing on either side of the linear axis. In addition circular diffraction zones may be provided to give both spherical and cylindrical power for astigmatism correction.

19 Claims, 4 Drawing Sheets

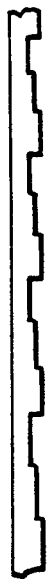
Fig.3a.   Fig.3b.   Fig.3c.
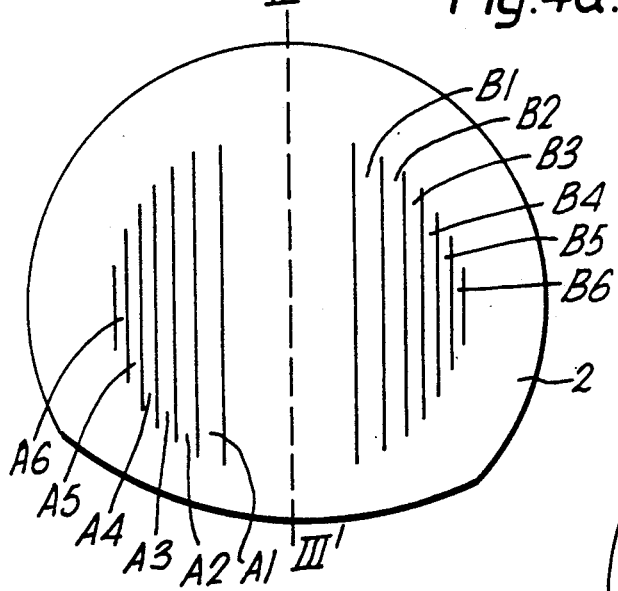
Fig.4a.
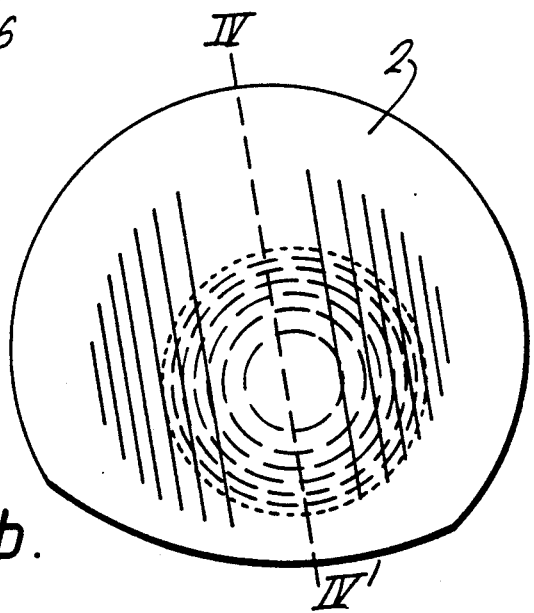
Fig.4b.

DIFFRACTIVE OPHTHALMIC LENS FOR CORRECTING ASTIGMATISM

This invention relates to an artificial eye lens in which at least a part of the optical power of the lens is obtained using diffractive means. By the term "artificial eye lens" is meant an artificial lens which in use is disposed against the eye or within the eye. Thus one particular type of artificial eye lens is a contact lens which is used against the eye to assist the action of the natural eye lens, and another is an intra-ocular which is inserted in the eye to replace the natural eye lens.

BACKGROUND OF THE INVENTION

The use of diffractive effects in optics and electromagnetic and similar radiant energy systems is well known. Diffraction gratings have been known for many years and more recently holographic gratings have become available. Such gratings disperse the incident light according to its wavelength. Essentially all that is needed to do this is a regularly spaced array of slits. The width of each slit as a proportion of the opaque separation distance between adjacent slits has a critical effect on the optical action. The emergent light is diffracted so that as well as some of its energy continuing as before, a proportion is deviated to either side of the unaffected beam and at a series of angles or "orders" which relate to the spacing of the slits and the wavelength of the light. Such arrays of slits are known as amplitude gratings. Alternatively, the slit plus space distance can be made to allow the incident light to pass through but impose some phase difference over a proportion of this distance. As long as each pattern is regularly and accurately repeated over the whole grating this will allow the dispersive effects to build up. This type of grating is known as a "phase grating".

Diffractive lenses have received far less attention than diffraction gratings. A normal lens deviates light from a circle within its aperture by a constant angle to a point somewhere along the axis. The slits and spaces of a diffraction grating have therefore been made circles to achieve a form of diffractive lens.

However if one simply forms a series of annular slits or zones with slit and space widths of equal dimensions or with the slit and space dimensions imposing a phase difference, this will give the effect of producing a large number of focal powers and generate images for each of them. This is because, unlike the diffraction grating where the extra orders emerge at different angles, the extra orders in the case of the annular arrangement occur along its axis giving images at different focal distances. Such annular arrangements are known as Zone Plates. We have already described a different arrangement in GB 2 129 157 namely a diffractive lens which generates two images one by refraction and one by diffraction and can effectively be used as a bifocal artificial eye lens. We have now found that an additional advantageous form of diffractive lens is one which can correct for astigmatism by means of the diffractive effect by having the capability of diffracting light predominantly into one order at one orientation. Such a lens can be used as an artificial eye lens in the form of both intra-ocular lenses and contact lenses.

A diffractive lens, according to the present invention can be made to behave in the same manner as both a refractive cylindrical lens and a refractive lens with a toric surface. A toric surface is one which at every part of its surface has maximum and minimum curvatures orthogonal to one another. A spherical surface is in fact a special case of the toric surface where the maximum and minimum curvatures are equal. A cylindrical surface is one in which the minimum curvature is zero, and a flat surface is one where maximum and minimum curvatures are both zero.

In a refractive cylindrical lens, the axis of the cylinder, part of which forms the lens surface is parallel to the principal meridian which has zero curvature. This meridian is known as the cylinder axis. A refractive cylindrical lens with a vertical cylinder axis will produce a line image parallel to the cylinder axis. A toric refractive lens will form two line images. Thus if one has a refractive lens with a toric surface having powers for example +6D and +4D, one can achieve the same effect by using a +4D thin spherical lens in contact with a thin cylindrical lens of +2D power. Other ways of achieving the same effect are by using (a) a +6D thin spherical lens in contact with a thin cylindrical lens of −2D power and (b) so called crossed cylinders by using two cylindrical lenses of powers +6D and +4D with their cylinder axes at right angles.

Diffractive lenses can be made which emulate the optical effect of a refractive cylindrical lens and of combining lenses in the manner just described so that astigmatism can be corrected by diffraction. Spherical power can be provided by normal refractive methods and lenses can also be made in which at least some of the spherical power of the lens is provided by means of rotationally symmetrical diffraction zones as disclosed in GB 2 129 157. It has further been found that a combination of the control of astigmatism by diffracting light into predominantly one order in one orientation, with the provision of spherical power in the manner disclosed in GB 2 129 157 in one lens enables presbyopes with astigmatism to wear contact lenses in which any astigmatism correction is also produced by diffraction.

SUMMARY OF THE INVENTION

Our invention includes an artificial eye lens in which the optical power of the lens is at least partially obtained by utilising the diffractive effect, and at least a part of that diffractive effect is utilised to enable the lens to have amongst its functions the ability to emulate a toric or cylindrical lens.

An artificial eye lens according to the invention comprises a lens body and at least one diffractive means for diffracting light predominantly into one order at one orientation, said diffractive means being formed as a series of substantially linear parallel zones whose zone spacings diminish either side of a linear axis. Preferably the diffractive means is a surface relief hologram.

An alternative way of obtaining a surface relief hologram with the desired orientation is to use a series of substantially linear zones defined by concentric ellipses, and our invention includes artificial eye lenses formed in this manner. The aspect ratio of the ellipses for such a lens is at least 2:1, and may be as high as 10:1, though we prefer to operate at aspect ratios of 5:1 or greater.

As indicated above it is also possible to provide one lens to replace two cylindrical lenses where two cylindrical lenses are used together to give the equivalent of a spherical or sphero-cylindrical lens. Sphero-cylindrical lenses are used in correcting astigmatism.

Our invention also includes an artificial eye lens which comprises a lens body and two diffractive means in which there is provided at a first orientation, diffractive means to diffract light predominantly into one order, and at a second orientation angled to said first orientation diffractive means to diffract light predominantly into one order. Useful optical effects are unlikely to be obtained within an acute angle between the orientations of less than 10 degrees. Preferably each said one order is a first order and the first order chosen may be the same in both cases, or may be +1, i.e. the positive first order in one case, and −1 i.e. the negative first order, in the other.

Our preferred arrangement when two diffractive means are used is one in which an artificial eye lens is formed so that the diffractive means are substantially at right angles to one another.

The means to diffract light can as before be a surface relief hologram formed as a series of linear parallel zones whose zone spacings diminish either side of a linear axis giving a line focus or alternatively a hologram formed by concentric ellipses with a high aspect ratio. The effect of two lenses may be obtained by using a pair of surface relief holograms arranged with their linear axes substantially at right angles to one another.

Because of finite manufacturing errors it is unlikely that diffractive means with exactly equal cylinder powers at exactly right angles can be made on a consistent basis. However a maximum deviation of the order of two degrees from exact equivalence is acceptable for most commercial purposes.

According to the invention, there is also provided, a bifocal artificial eye lens with an astigmatism correction, having both spherical and cylindrical power derived from diffractive means by combining substantially linear diffraction zones and rotationally symmetrical diffraction zones.

There is further provided a bifocal artificial eye lens with an astigmatism correction which comprises a lens body provided with both spherical and cylindrical power by providing superimposed on one another two diffractive means, a first means in the form of substantially linear zones, and a second means in the form of substantially circular zones.

An arrangement in which light is diffracted into predominantly one order is achieved by ensuring that each zone, spacing or slit is shaped so that the light is refracted in a manner that the direction of maximum intensity of light from each individual zone coincides with a direction which will result in the light constructively interfering across all the zones. The directions in which light constructively interferes are known as orders of diffraction and may act in a positive and negative manner either side of the undeviated direction. The positive and negative first orders (+1 and −1) occur when the phase difference at the edge of each zone is equal to the design wavelength. Higher orders require 2, 3 or more wavelengths and are of less practical use because the necessary manufacturing precision to use such orders is difficult to achieve and unwanted optical effects at other wavelengths become more obtrusive. We prefer therefore to asymmetrically shape the zones so as to obtain light at a first order of diffraction although other orders are feasible.

Orientation may be explained by reference to optical systems exhibiting cylindrical power. A cylindrical surface provides such power and has the ability to form from a point object, a line image which is oriented parallel to the axis of the cylindrical surface. However to form this line the light has been deviated in the orthogonal plane. In lens systems which also contain spherical power, two line foci may be obtained and the cylindrical component is the difference between these. The same effect can be obtained by refraction using a toric surface. The common feature of cylindrical and toric surfaces is the concept of different optical effects from different orientations across the aperture of the optical surface or system. This creates an axial astigmatic effect. Thus in the case of the present invention, the use of a series of linear parallel zones on a lens in which the zone spacing diminishes either side of the linear axis results in a line focus similar to a cylindrical lens. Thus the distance $d_n$ of each zone edge from the central axis is given substantially by:

$$d_n = j\sqrt{n}$$

where n is an integer number 1, 2, 3, 4, 5 etc and j is some constant. Variations from this formula give rise to aberrations of a greater or lesser effect and may be useful to fine tune the quality of image formed by the diffractive lens and any associated lens system e.g. the eye.

Considering the application of the present invention in the field of contact lenses, the correction of astigmatism by corneal lenses at present divides into two methods. In the case of rigid lenses, such as rigid gas permeable lenses, the lens tends to vault the toric form of the cornea from which the astigmatism results and present a spherical surface thus masking corneal astigmatism up to about 2 dioptres. However it is not possible by this means to correct for lenticular astigmatism, and contact lens wearers needing such a correction must be fitted with a contact lens which fits the toric form of the cornea. For such a contact lens to have the proper corrective effect on the astigmatism of the eye, it must rest on the eye in the correct orientation. For this they are usually made so that a part of their periphery is heavier so that the lens is ballasted on the eye and ideally takes up the correct orientation on the eye. Thus the fitting of a contact lens to correct astigmatism has to take account of a number of interacting features, which include the cylinder power, the cylinder angle, and the basic power and physical shape of the eye contacting surface of the lens. The invention can be implemented to conventional stabilisation techniques such as lens with truncation, ballast, thin zone, flange, slab-off, or toric peripheral curve methods. This is done by applying the astigmatism correction or providing the cylindrical power by diffractive means at the desired orientation whichever stabilisation technique is used. In a preferred form, the required correction is applied to a lens whose back surface has a toric shape such that it will take up a particular orientation on the eye of the end-user. In practice, a patient would be fitted with a series of lenses from a trial set to find the best fit. It would then be arranged for the required cylinder power correction to be generated on a lens of the same shape and design as the best fit from the trial set. Because the diffractive means can be applied without altering the basic orientation controlling shape of the lens, the lens when supplied will correct effectively because it will have been corrected according to the known orientation on the eye which will not change.

Our invention also includes a method of forming an artificial eye lens body for use in the treatment of astigmatism comprising providing on said lens body diffractive means capable of diffracting light predominantly into one order at one orientation.

A further artificial eye lens body according to the invention is one for use in correcting astigmatism in which at least one diffractive means is provided for diffracting light predominantly into one order at one orientation.

There is also provided according to the invention, a method of providing correct vision for a person suffering from astigmatism comprising fitting said person with a lens which comprises a lens body and at least one diffractive means formed as a series of substantially linear parallel zones whose zone spacings diminish either side of a linear axis.

BRIEF DESCRIPTION OF THE DRAWINGS

FIGS. 3a, 3b and 3c show in cross section various prior art methods of shaping zone profiles which may be implemented in shaping the zones used in the lenses of the present invention.

FIG. 4a is a schematic representation of a single vision contact lens with an astigmatism correction according to the present invention.

FIG. 4b is a schematic representation of a bifocal diffractive contact lens with an astigmatism correction according to the present invention.

DESCRIPTION OF THE PREFERRED EMBODIMENTS

Figure 1A:
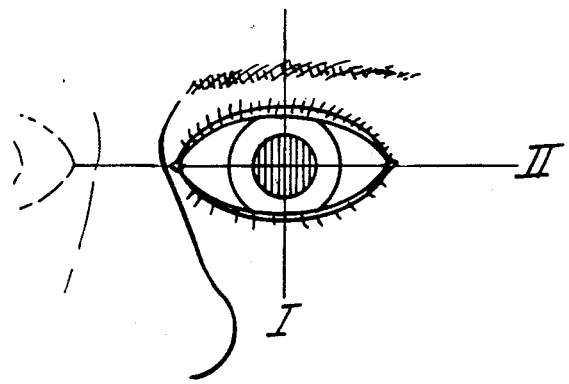
FIGS. 1a, 1b and 1c are representations of an eye wearing a contact lens, in accordance with the invention, 1b and 1c showing respectively a cross section in each of two planes I and II through the lens.
Figure 1B:
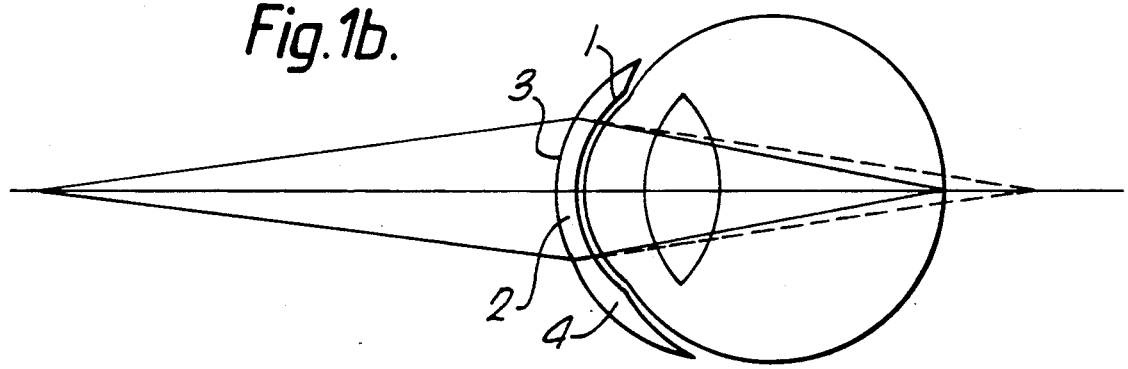
Figure 1C:
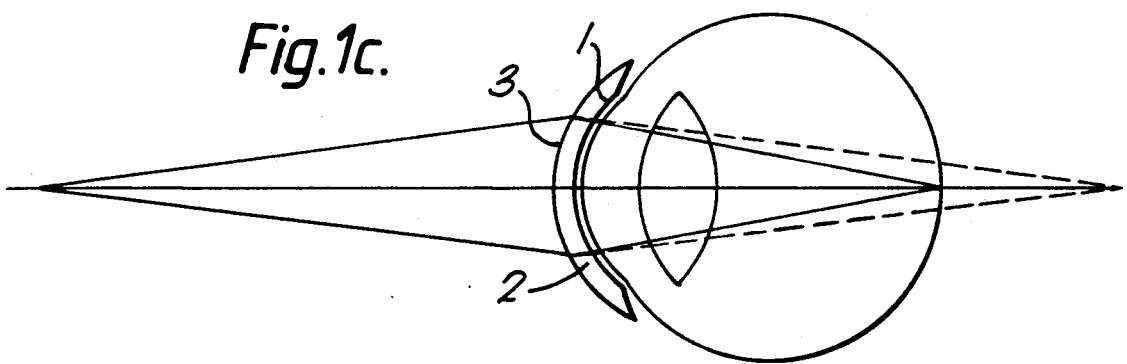
Figure 2:
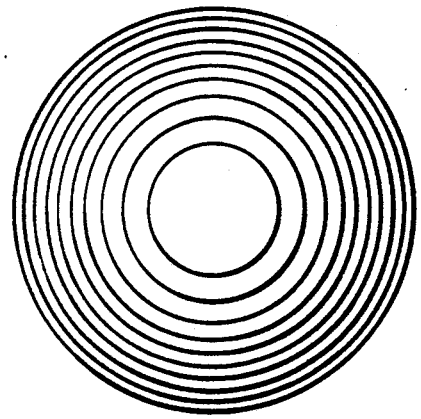
FIG. 2 schematically represents concentric zones of a prior art diffractive lens, which generates two images, one by refraction and one by diffraction.
Figure 6:
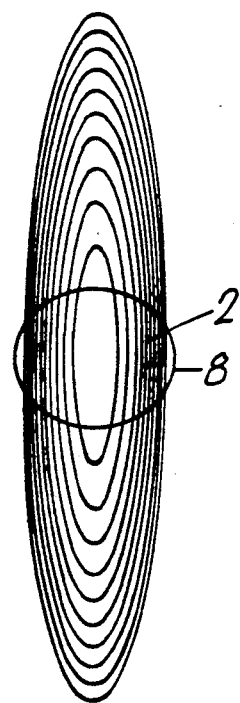
FIG. 6 is a schematic representation of how by generating zones on the basis of following a pattern represented by high aspect ratio elipses, a diffractive lens with an optical effect emulating a cylindrical lens can be formed, the area of the lens body being indicated by the line 8.

Referring initially to FIGS. 1a, 1b and 1c a typical adult human eye cornea has a radius of curvature of 8 mm. Accordingly the rear surface 1 of a well fitting contact lens 2 has a radius of curvature near this value. The front surface 3 of the contact lens has a radius of curvature which can vary from 6 mm to 12 mm depending on the refractive correction required by the wearer, which may be from +20 dioptres to −20 dioptres. The lens 2 can thus have refractive power from the material (refractive index) of the lens and the curvature of its front and rear surfaces 3 and 1. In the case of a bifocal contact lens additional positive power is required to replace the failing accommodation of the presbyopic wearer. This may vary from 0.5 dioptres to 3 or even 4 dioptres depending on the needs of the wearer and the amount of residual accommodation still available; a value of 2 Dioptres can be considered as illustrative for general purposes. Such additional power can be provided by diffraction, and in particular by providing the lens 2 with a plurality or series of concentric zones arranged to diffract light transmitted through the lens in the manner of a phase zone plate. Our GB Specification 2 129 157A describes how to manufacture lenses in which such additional positive power is provided by diffraction and such a lens is shown in FIG. 2.

As indicated above the present invention provides a means of correcting astigmatism by the use of diffractive means. In this situation, the cornea is rarely spherical i.e. the radius of curvature on the vertical axis is not the same as the radius of curvature on the horizontal axis. The lens must be properly oriented on the eye and this may be done e.g. by ensuring that the back surface of the lens matches the curvature of the cornea to such an extent as to allow the lens to adopt a fixed or known orientation on the cornea. In this way, the shape can be designed to get the best possible fit, and the correction added by introducing cylindrical power by means of a diffractive effect. The diffractive power required is of the order of 1 to 3 dioptres, and as shown in FIGS. 4a and 4b is achieved by a series of linear zones.

FIG. 4a shows a single vision lens with a lens body 2 provided in a conventional manner in which the correction for astigmatism according to the invention is provided by a series of linear zones numbered A1 to A6 and B1 to B6. A bifocal lens with both spherical and cylindrical power derived from diffractive means is obtained when linear zones and circular zones are combined as shown in FIG. 4b. In both the lenses shown, the linear zones may be created with their surfaces in any of the forms shown in FIG. 3.

A simplified formula for determining the position of the outer edges of each linear zone is $$Y_n^2 = 2nf\lambda$$

where $Y_n$ is the distance from the central axis III/III' of the lens to the zone edge, f is the focal length of an equivalent cylindrical lens, $\lambda$ is the design wavelength, and n is the number of the zone away from the axis. In order to adjust the quality of the image, it may be advantageous in some cases to provide some correction for aberration. One way of doing this would be to change the power value to which $Y_n$ is raised to some other value such as 2.03 or 1.95. As the human eye exhibits spherical aberration, a further alternative would be to employ an expression such as $Y_n^2 + KY_n^4 = 2nf\lambda$. The value of K is preferably substantially less than 1 and serves to modify the zone edge position values by amounts generally within 10% of their values given by the simplified formula. Departures in excess of 10% of these values will be needed in the situation where compensation is required for greater amounts of regular or irregular aberrations which can be then counteracted by the diffraction effect. The spacings of the linear zones for the correction of 1.0 dioptres of astigmatism (assuming a design wavelength of 555 nm, the peak for human visual response) are as follows:

| | | |
|---|---|---|
| Outer edge of zone | +11 | 3.49 mm |
| | +10 | 3.33 |
| | +9 | 3.16 |
| | +8 | 2.98 |
| | +7 | 2.79 |
| | +6 | 2.58 |
| | +5 | 2.36 |
| | +4 | 2.11 |
| | +3 | 1.82 |
| | +2 | 1.49 |
| | +1 | 1.05 |
| Centre line of linear zones | | 0.0 |
| | −1 | −1.05 |
| | −2 | −1.49 |
| | −3 | −1.82 |
| | −4 | −2.11 |
| | −5 | −2.36 |
| | −6 | −2.58 |
| | −7 | −2.79 |
| | −8 | −2.98 |
| | −9 | −3.16 |
| | −10 | −3.33 |
| | −11 | −3.49 |

Thus covering an overall optic diameter of 6.98 mm.

These sizes will be changed for other astigmatic correction values. For 2.0 dioptres of astigmatism correction twice as many zones will be needed over the same aperture and for 3.0 dioptres, 3 times as many over the same aperture. For the larger corrections it is possible to use fewer zones particularly towards the edge of the required aperture by arranging that the zone width covers the same spacing as two adjacent zones of those indicated in FIG. 4a with a step height or effective phase effect which is increased to include the missing zone. This then uses the second order producing substantially the same optical effect as the previous two adjacent zones.

In the case of 2.75 dioptre cylinder correction for light with a principal wavelength of 555 nm, the spacing would be $Y_1 = 0.635$ mm
$Y_2 = 0.898$
$Y_3 = 1.100$
$Y_4 = 1.271$
$Y_5 = 1.421$
$Y_6 = 1.556$
$Y_7 = 1.681$
$Y_8 = 1.797$
.
.
.
$Y_n$ where $Y_1$ is the distance from the central axis of the lens to the first zone edge, and $Y_2$ is the distance from the same point to the second zone edge, and so on for each value of Y. The same values also occur on the other side of the central axis. The figures below show the values for a 3 dioptre cylinder correction with a principal wavelength at 600 nm.

$Y_1 = 0.632$ mm
$Y_2 = 0.894$
$Y_3 = 1.095$
$Y_4 = 1.265$
$Y_5 = 1.414$
$Y_6 = 1.549$
$Y_7 = 1.673$
$Y_8 = 1.789$
.
.
.
$Y_n$

The figures below show the Y values for a 2 dioptre cylinder lens at 555 nm.

$Y_1 = 0.745$ mm
$Y_2 = 1.054$
$Y_3 = 1.290$
$Y_4 = 1.490$
$Y_5 = 1.666$
$Y_6 = 1.825$
$Y_7 = 1.971$
$Y_8 = 2.107$
.
.
.
$Y_n$

One way of providing e.g. that light is predominantly directed into the positive first order at expense e.g. of transmission at the negative first order is by dividing each zone into three equal areas and arrange a staircase effect on the phase of light. This is shown in FIG. 3a. The phase difference between each step must now be equivalent to $\lambda/3$ where $\lambda$ is the design wavelength. In this case, it is possible to calculate that 68% of the light intensity will arise from the positive first order. If one divides the zones into four areas, the phase difference between each step is now equivalent to $\lambda/4$ and 81% of the light intensity will arise from positive first order. Thus as one increases the number of steps in the staircase of phase delay over each zone width, the action is to direct more and more of the light into the positive first order diffraction image. As more and more steps such as shown in FIG. 3b are introduced the overall shape of the contour becomes equivalent to a curve so that the total change in phase at the edge of the zone will be $\lambda$. We prefer to use the arrangement as shown in FIG. 3c, where the overall shape of the contour of each zone is formed as a smooth curve. However manufacturing techniques may leave a stepped profile which approximates to the smooth curve. Manufacturing errors may also preclude a precisely vertical step at the edge of each zone as shown in these drawings. Some degree of rounding of this edge has little effect on the intensities of the diffractive order.

The negative first order occurs when the steps or smooth curve are formed in the opposite direction. The definition of +1 order and −1 order is arbitrary although the negative order usually describes a divergent effect and the positive order a convergent effect.

The use of two cylindrical lenses with their axes at right-angles to give substantially an equivalent spherical or sphero-cylindrical lens is well known in optics and optometry. Our invention also includes the use of two linear-zone diffraction lens profiles on the same or the closely adjacent surfaces of the lens to give substantially a spherical or sphero-cylindrical lens. (In optics and optometry surfaces which have a sphero-cylindrical power are also known as toric surfaces). When the required effect is that of a spherical lens, the linear-zone diffractive lenses must have the same optical effect (power) and be orientated at right angles. However, it may be that an optical system providing overall spherical power may generate some of this with a diffractive equivalent of a toric lens and a real refractive toric lens to provide a total system having no cylindrical component.

Figure 5A:
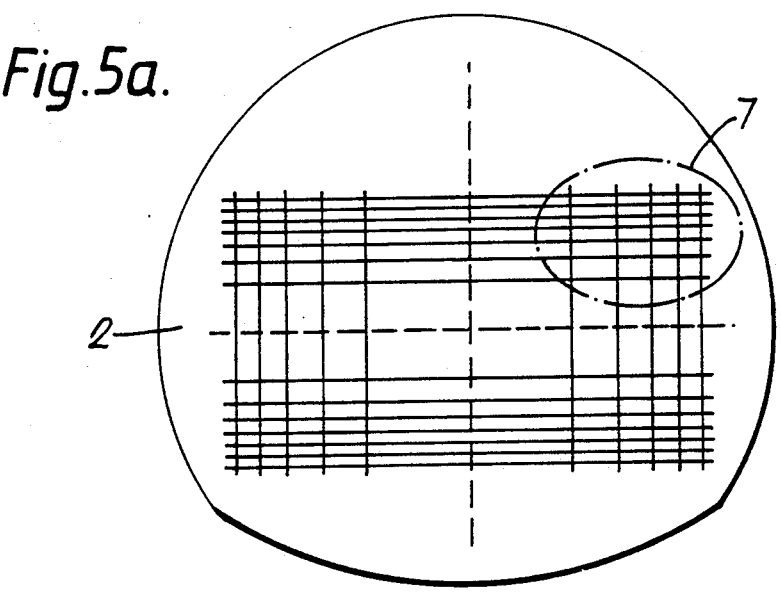
FIG. 5a is a schematic representation of the zone edge locations for a diffractive lens equivalent in optical effect to the optical effect produced by combining a pair of cylindrical lenses.
Figure 5B:
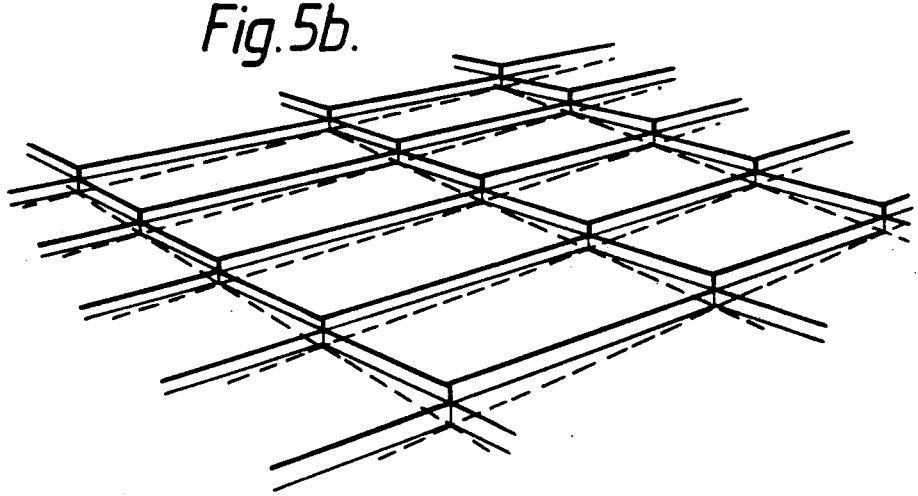
FIG. 5b is a perspective view of the area 7 of FIG. 5a where the zone surface is smooth. The underlying surface which may be flat, curved convex or curved concave is indicated by the dotted lines.
Figure 5C:
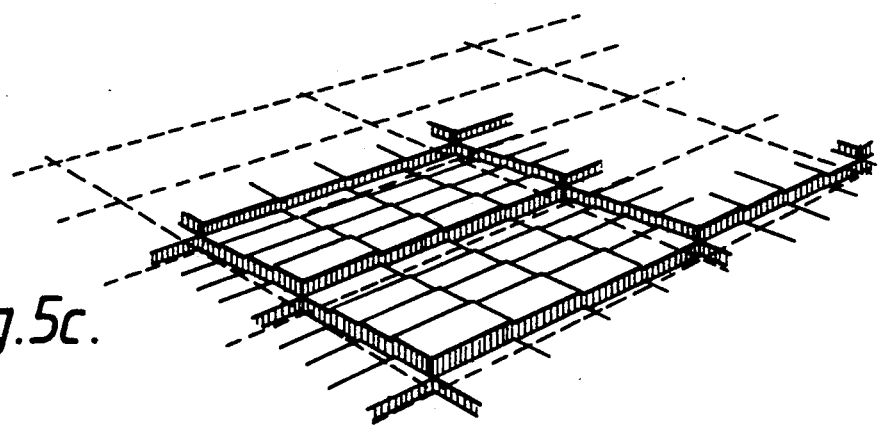
FIG. 5c shows the same perspective view of the area 7 of FIG. 5a where instead of using a smooth surface for the zones a stepped surface is used, each step of which is $\lambda/4$ in height. This surface approximates to the smooth surface where the discrepancy from that required does not have an optical effect exceeding $\lambda/4$.

FIG. 5a shows two linear-zone diffractive means on the same surface at right angles but having different optical powers. This means the zone widths are significantly different and the concept can be seen more clearly in FIG. 5b. As indicated above, because of manufacturing tolerances it is not cost effective to try and achieve exactly equal powers at exactly right angles. At the design wavelength the step sizes have been chosen to create one wavelength of phase difference by changing in a relatively abrupt fashion the profile of the surface, although this could also be achieved by refractive index changes. The surface profile effect is rather easier to illustrate and the area 7 on FIG. 5a is shown in a perspective view given in FIG. 5b. The diffractive effects of this structure are to direct the majority of the light energy or other radiant energy at a compound angle between those expected by the linear-zone diffractive profiles when considered independently. The underlying flat or smoothly curved surface is shown by the dotted lines. The surface of the steps are therefore tilted with respect to this underlying surface. If this smooth surface is approximated by a series of interstitial steps it gives the same optical effect as indicated above. This surface would then appear (for the step approximation) as shown in FIG. 5c.

Lenses according to the invention may be made by the direct cutting of the surface using a high precision lathe. The cutting point is often a single point diamond and surfaces of good optical quality can be achieved. Such lathes have computer control systems which can position the cutting diamond to within one micron and can return centre of rotation of the diamond carrying arm to the same position within ±0.2 microns, e.g. a lathe set up to turn a radius of 9 mm could be shifted at each zone edge by the one wavelength delay step size and continue cutting the 9 mm radius until the second zone edge, etc. A computer controlled lathe with secondary motion can for example be used in a fly-cutting mode with an offset preform. They can also be made using laser ablation and a suitably shaped mask.

As described above the diffractive means is a series of hills (or valleys) i.e. a surface relief hologram, on e.g. the rear surface. It will be appreciated that a surface relief hologram could instead be on the front surface of the lens. It will further be appreciated that the diffractive power could alternatively be provided by refractive index changes, or by a combination of refractive index and thickness changes. In each case the changes should be such as to provide the required diffraction. Yet further, although lenses are described above as having refractive power resulting from the material of the lens and the basic curvature of its surfaces, lenses could have zero refractive power so that their optical power is wholly diffractive. Still further, although the order of diffraction into one sign (described above as positive) of which light of the design wavelength is predominantly directed is preferably the first order, some other order could be employed with the lens appropriately designed predominantly to direct light of the design wavelength into one sign of that other order of diffraction. Although the above description in terms of ophthalmic lenses has been primarily directed to describing the application of the invention to the design and manufacture of contact lenses, lenses employing the same diffractive effects may be formed as intra-ocular lenses for implantation in the eye as a replacement for the natural lens.

I claim:

1. An artificial eye lens comprising a lens body and at least one diffractive means for diffracting light predominantly into one order at one orientation, said diffractive means being formed as a series of substantially linear parallel zones whose zone spacings diminish either side of a linear axis.

2. An artificial eye lens as claimed in claim 1 in which the substantially linear parallel zones are defined by concentric ellipses.

3. An artificial eye lens according to claim 2 in which said ellipses have an aspect ratio of at least 5:1.

4. An artificial eye lens according to claim 1 comprising a lens body with two diffractive means in which there is provided at a first orientation diffractive means to diffract light predominantly into one order, and at a second orientation angled to said first orientation diffractive means to diffract light predominantly into one order.

5. An artificial eye lens as claimed in claim 4, in which the diffractive means are substantially at right angles to one another.

6. An artificial eye lens as claimed in claim 4 in which each said one order is a first order.

7. An artificial eye lens as claimed in claim 6 where the first order is the same sign in both cases.

8. An artificial eye lens comprising a lens body according to claim 1 in the form of a contact lens.

9. An artificial eye lens comprising a lens body according to claim 1 in the form of an intra-ocular lens.

10. A bifocal artificial eye lens with an astigmatism correction having both spherical and cylindrical power derived from diffractive means by combining substantially linear diffraction zones and substantially circular diffraction zones.

11. An artificial eye lens comprising a lens body according to claim 10 in the form of an intra-ocular lens.

12. An artificial eye lens comprising a lens body according to claim 10 in the form of a contact lens lens.

13. A bifocal artificial eye lens with an astigmatism correction comprising a lens body provided with body spherical and cylindrical power by providing superimposed on one another two diffractive means, a first means in the form of substantially linear zones, and a second means in the form of substantially circular zones.

14. An artificial eye lens comprising a lens body according to claim 13 in the form of a contact lens.

15. An artificial eye lens comprising a lens body according to claim 13 in the form of an intra-ocular lens.

16. An artificial eye lens comprising a lens body whose optical power is at least partially obtained by means providing a diffractive effect, and wherein said means is operable to provide at least a part of that diffractive effect so as to enable the lens to have among its functions the ability to emulate a toric or cylindrical lens.

17. A method of forming an artificial eye lens body for use in the treatment of astigmatism comprising providing on said lens body diffractive means capable of diffracting light predominantly into one order at one orientation.

18. An artificial eye lens body for use in correcting astigmatism in which at least one diffractive means is provided for diffracting light predominantly into one order at one orientation.

19. A method of providing corrected vision for a person suffering from astigmatism comprising fitting said person with an artificial eye lens in which at least one diffractive means is provided for diffracting light predominantly into one order at one orientation.

* * * * *